United States Patent [19]
Lisak et al.

[11] Patent Number: 5,766,134
[45] Date of Patent: Jun. 16, 1998

[54] AUTOGENOUS BONE SPECIMEN COLLECTOR

[75] Inventors: Stephen P. Lisak; Larry L. Young, both of Arab, Ala.

[73] Assignee: Atrion Medical Products, Inc., Arab, Ala.

[21] Appl. No.: 503,520

[22] Filed: Jul. 18, 1995

[51] Int. Cl.$^6$ ............................................. A61B 10/00
[52] U.S. Cl. ............................................. 600/562; 604/320
[58] Field of Search ........................ 604/283, 36, 131–33, 604/317–321; 128/758, 749, 760; 210/232

[56] References Cited

U.S. PATENT DOCUMENTS

| | | |
|---|---|---|
| 3,661,144 | 5/1972 | Jensen et al. |
| 3,785,380 | 1/1974 | Brumfield. |
| 3,791,524 | 2/1974 | Cho .................................. 210/232 |
| 3,889,657 | 6/1975 | Baumgarten ..................... 128/758 |
| 4,083,706 | 4/1978 | Wiley. |
| 4,393,879 | 7/1983 | Milgrom. |
| 4,468,217 | 8/1984 | Kuzmick et al. |
| 4,801,292 | 1/1989 | Watson. |
| 4,834,703 | 5/1989 | Dubrul et al. |
| 4,870,975 | 10/1989 | Cronk et al. |
| 4,886,492 | 12/1989 | Brooke. |
| 4,957,492 | 9/1990 | McVay. |
| 5,108,381 | 4/1992 | Kolozsi. |
| 5,122,153 | 6/1992 | Harrel. |
| 5,244,458 | 9/1993 | Takasu. |
| 5,269,785 | 12/1993 | Bonutti. |
| 5,275,609 | 1/1994 | Pingleton et al. |
| 5,514,117 | 5/1996 | Lynn ................................. 604/283 |

OTHER PUBLICATIONS

*Surgical Dental Implants, Data from the 1991 Special Version–Survey of Dental Practice and the 1990 Survey of Dental Services Rendered*, pp. 1–15, American Dental Association, Copyright 1993.

*Vital And Health Statistics*, pp. 11–14, U.S. Department of Health and Human Services, Dec. 1992, DHHS Publication No. (PHS)93–1511.

*Primary Examiner*—Max Hindenburg
*Assistant Examiner*—Pamela L. Wingood
*Attorney, Agent, or Firm*—Trexler, Bushnell, Giangiorgi & Blackstone, Ltd.

[57] ABSTRACT

A collector unit for collecting tissue or bone from a dental patient during a dental implant procedure generally includes a cover member, a filter support member, a filter medium and a gasket member. The support member is mountable within the cover member with the gasket member positioned therebetween to form the unit. A passage is provided through the unit to allow the passage of fluid material through the unit. The support member has a pair of spaced-apart, opposed filter support arms for removably supporting a substantially flat section of filter medium so that the filter medium overlies the inlet passage such that fluid material passing through the unit must pass through the filter medium which will filter out any bone or tissue specimens. The filter medium is removable from the supporting structure so that it can be positioned in a flat-orientation to facilitate the removal of bone or tissue specimens therefrom. Once removed, the filter medium cannot be reattached to the supporting structure. A pair of latch arms releasably secure the cover member and the support member together. The gasket member provides an integral one-way valve which normally blocks the inlet passage and can be moved out of association with the inlet passage to provide a path for the flow of fluid material through the unit.

28 Claims, 2 Drawing Sheets

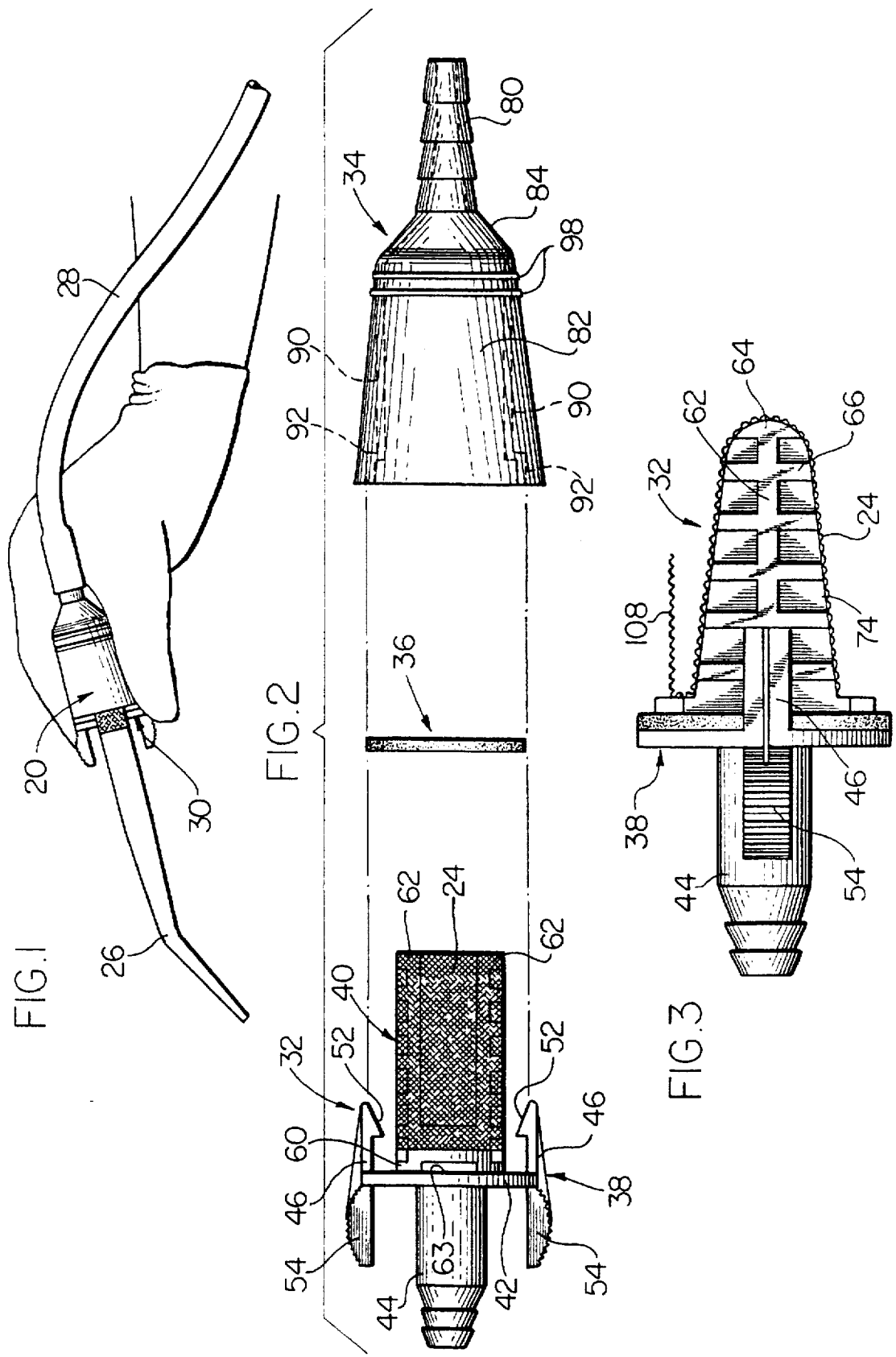

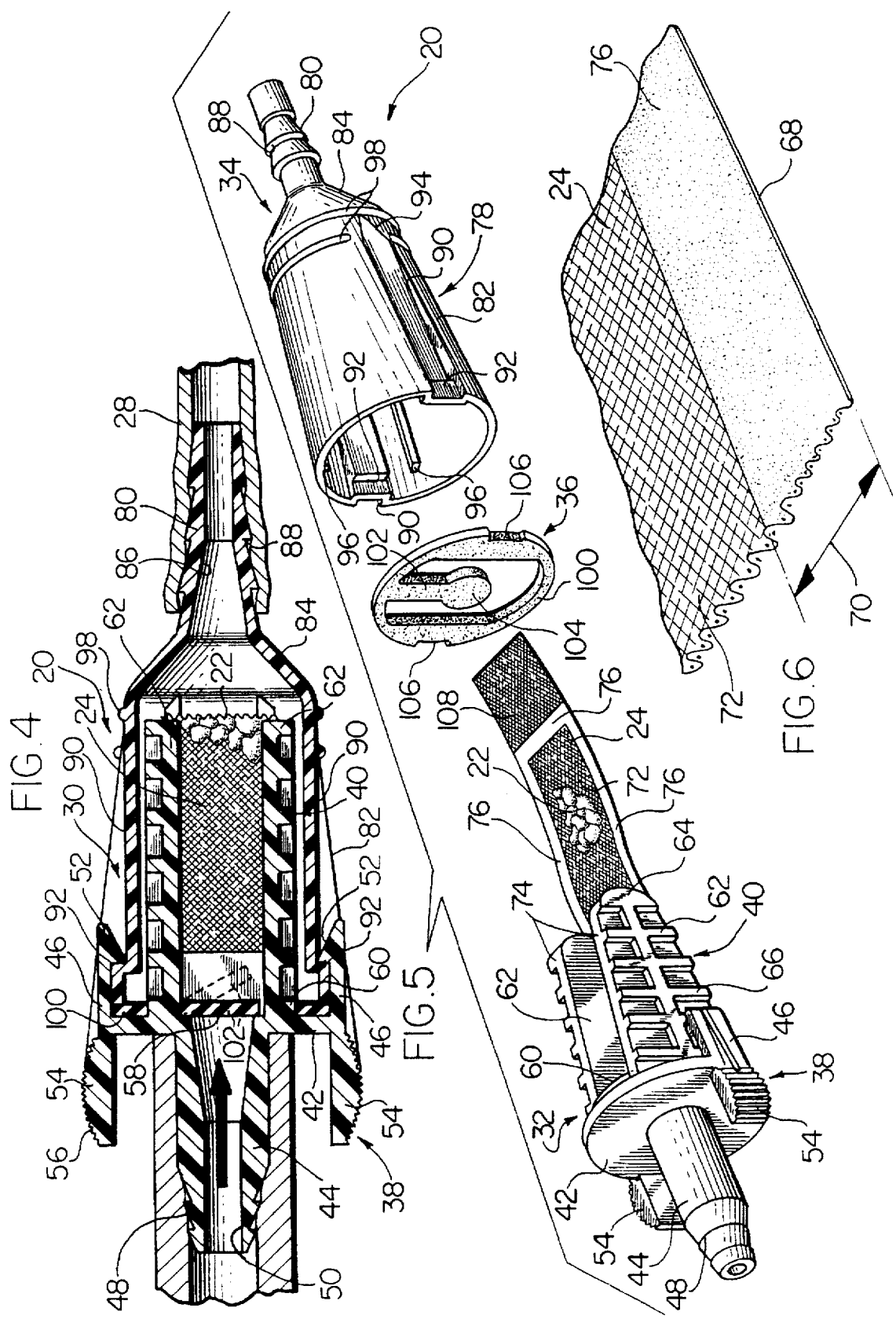

AUTOGENOUS BONE SPECIMEN COLLECTOR

BACKGROUND OF THE INVENTION

This invention is generally directed to a novel autogenous bone specimen collector, and more specifically to a specimen collector useful in the harvesting of bone removed from a jaw of a dental patient during a drilling procedure for a dental implant. The novel collector unit of the present invention may also be used for harvesting bone or other tissue specimens or the like from a patient or from alternate sites or any other material in a fluid.

Dental implants are commonly used to replace a tooth that had to be removed due to decay, fracture of the tooth or the like. Dental implants are particularly used in the replacement of molars where the molars are not adjacent to supporting tooth structure for a bridge. Currently, for all dental implants, the dentist or oral surgeon removes the tooth and then has to fit the implant into a hole or aperture in the patient's jaw made by drilling. During this drilling procedure, the dentist suctions out bone material and tissue from the drilling site as he or she drills. Thereafter, the implant, which is generally in the form of a post, is adhesively secured or otherwise mounted into the drilled aperture.

Quite often, the hole or aperture drilled for the implant is slightly larger than the implant and it is necessary to pack the hole with bone material to secure or support the implant in the hole. This bone material is generally purchased from a bone bank which harvests the bone material from cadavers. The bone material is expensive, with one small vial of bone material costing approximately $300.00. As such, it is preferable that the bone material drilled from the patient's own jaw during drilling be harvested or saved for use in securing the implant, not only for cost reasons, but also to prevent infection, as it is always best to use ones own tissue where possible. In addition, the chance of disease is reduced if the patients own bone material is used.

Several devices have been heretofore disclosed for collecting bone or tissue specimens from a patient. The bone or tissue specimens are collected in the device on a sterile filter. With these prior art devices, the collected specimens on the filter are difficult to remove from the filter and must be scraped off of the filter, due to the filter shape, by a tool.

The present invention discloses a novel collector unit which is used to harvest bone or tissue specimens from a patient. The bone or tissue specimens are collected on a sterile filter medium housed within the collector unit. After collection is complete, the filter medium can be easily removed from the collector unit and laid out in a flat disposition so that the bone or tissue specimens can be easily removed from the filter medium. Other features and advantages of the present invention will become apparent upon a reading of the specification herein.

OBJECTS AND SUMMARY OF THE INVENTION

A general object of the present invention is to provide a novel collector unit that is used to harvest bone or tissue specimens from a patient.

An object of the present invention is to provide a novel collector unit that collects bone or tissue specimens on a sterile filter medium, which filter medium can be easily removed from the collector unit and laid flat so that the bone or tissue specimens can be easily removed or scraped off of the filter medium.

Yet another object of the present invention is to provide a novel collector that collects bone or tissue specimens on a sterile filter medium, which filter medium can be easily removed from the collector unit and cannot be reattached or reassembled with the collector unit after the filter medium has been detached from the collector unit.

Another object of the present invention is to provide a novel collector unit having a filter medium therein, which unit can be easily disassembled to allow an operator to remove the filter medium therefrom, even when the operator is wearing wet gloves.

A further object of the present invention to provide a novel collector unit for use in a suction line; the unit having gasket member therein that prevents the use of the collector unit if the unit is incorrectly oriented in the suction line.

Yet a further object of the present invention to provide a novel collector unit which has a "snap-fit" attachment structure for securing parts of the collector unit together.

Briefly, and in accordance with the foregoing, the present invention discloses a novel collector unit for collecting bone specimens during a surgical procedure. For example, bone specimens can be collected by the collector unit from a dental patient during the drilling of an aperture in the patient's jaw for the mounting of a dental implant device. The collector unit can be used as a unit in the suction line or can be incorporated into the design of the aspirator tip. The collector unit can be used in a variety of applications, including, for example, tissue collection. The novel collector unit of the present invention generally includes a housing assembly provided by an outer cover member, an inner filter support member, a substantially planar filter medium and a gasket member.

The filter support member is mountable within the cover member. The filter support member may include a fluid inlet passage therethrough and the cover member includes a fluid outlet passage therethrough to provide a passage through the collector unit for fluid material containing bone specimens to be filtered out by the filter medium from the remainder of the fluid material.

The filter support member includes a filter supporting structure, which includes a pair of spaced-apart, opposed filter support arms, for supporting and securing thereto the filter medium in a position which is disposed about or spanning an inner portion of the inlet passage such that fluid material passing through the collector unit must pass through the filter medium which will filter out any bone specimens in the fluid material. The filter medium is preferably planar and removable from the filter supporting structure so that it can be positioned in a flat-orientation to facilitate the removal of bone specimens from the filter medium. Once the filter medium is detached from the filter supporting structure, the filter medium cannot be easily reattached or resecured to the filter supporting structure. The filter medium may include a tab portion which is not secured to the filter support arms so that an operator can easily remove the filter medium from the filter support arms.

A pair of "snap-fit" latch arms are provided on the filter support member for releasably securing the cover member and the filter support member together. The latch arms include a finger engaging portion and a shoulder portion thereon. The shoulder portion on each latch arm engages with a raised shoulder formed in an elongated slot in the cover member to releasably secure the cover member and the filter support member together. The shoulder portion on each latch arm is movable out of engagement with the raised shoulder to allow the cover member and the filter support 5,766,134

3 member to be easily separated from each other so that the filter medium can be removed from the filter support member.

Each finger engaging portion, each of which has a plurality of ridges thereon, can be pressed inwardly to move each shoulder portion out of engagement with the associated raised shoulder. The ridges allow an operator to easily grasp the finger engaging portions, even when the operator is wearing wet gloves. The cover member may include a plurality of grip rings thereon so that an operator can easily grasp the cover member even when the operator is wearing wet gloves to separate the cover member and the filter support member from each other.

The gasket member seals the juncture between the filter support member and the cover member and also provides a one-way valve to prevent the operation of the collector unit when it is placed in the incorrect direction in the suction line. The gasket member includes an outer portion which is positioned between the filter support member and the cover member and a tongue portion which depends inwardly from the outer portion and covers the end of the fluid inlet passage to block the flow of fluid material through the collector unit. The tongue portion is moved out of association with the fluid inlet passage to provide a path for the flow of fluid material through the collector unit when fluid material flows through the unit in a proper direction.

BRIEF DESCRIPTION OF THE DRAWINGS

The organization and manner of the structure and operation of the invention, together with further objects and advantages thereof, may best be understood by reference to the following description, taken in connection with the accompanying drawings, wherein like reference numerals identify like elements in which:

FIG. 1 is a perspective view of a novel autogenous bone specimen collector unit which incorporates the features of the invention, such unit being incorporated for use in a suction line and being held by an operator's hand;

FIG. 2 is an exploded, side elevational view of the novel autogenous bone specimen collector unit shown in FIG. 1, showing the elements of the unit which include a housing assembly including a filter support member having a filter medium attached thereto, a gasket member and a cover member;

FIG. 3 is a top elevational view of the filter support member having the filter medium attached thereto;

FIG. 4 is a cross-sectional view of the autogenous bone specimen collector unit in an assembled condition and connected in a suction line;

FIG. 5 is an exploded, perspective view of the novel autogenous bone specimen collector unit showing the filter support member having the filter medium partially detached therefrom, the gasket member and the cover member; and FIG. 6 is a partial, perspective view of the filter medium used in the present invention.

DETAILED DESCRIPTION OF THE PREFERRED EMBODIMENT

While the invention may be susceptible to embodiment in different forms, there is shown in the drawings, and herein will be described in detail, a specific embodiment with the understanding that the present disclosure is to be considered an exemplification of the principles of the invention, and is not intended to limit the invention to that as illustrated and described herein.

4

The present invention discloses a novel specimen collector unit 20 and positioned flat for harvesting bone specimens 22 from a patient. The bone specimens 22 are collected on a sterile filter medium 24 which is housed within the unit 20 as described herein. The filter medium 24 can be easily removed from the unit 20 so that an operator can easily remove the harvested bone specimens 22 from the filter medium 24. While the novel collector unit 20 of the present invention is described herein with reference to usage as harvesting bone specimens 22 from a patient, such as a dental patient during drilling in preparation for a dental implant, it is to be understood that the novel collector unit 20 can also be used in a variety of different applications, such as collecting or harvesting tissue specimens or the like from a patient or any other material in a fluid.

The collector unit 20 may be used as an in-line unit for usage in a suction line with a number of different aspirator tips 26 so that the bone specimens 22 are directly collected from the aspirator tip 26 onto the sterile filter medium 24. The collector unit 20 can be plugged directly into the aspirator tip 26, as shown in FIG. 1, or a short piece of tubing (not shown) may be added between the aspirator tip 26 and the collector unit 20, if required. The opposite end of the collector unit 20 has a longer hose 28 attached to a suction pump (not shown). Alternatively, the collector unit 20 could be incorporated into the aspirator tip itself.

Directing attention to FIG. 2, the novel collector unit 20 of the present invention is formed from a housing assembly 30 which includes an inner filter support member 32 and an outer cover member 34 which are releasably attached together. The flat or planar filter medium 24 is releasably secured to the filter support member 32, as described herein. A gasket member 36, which seals the housing assembly 30 and also functions as an integral one-way valve, is provided between the filter support member 32 and the cover member 34 when the support member 32 and cover member 34 are attached together, as described herein. While a preferred embodiment of the invention is illustrated wherein the filter support member 32 includes the inlet passage for the housing assembly 30, and the cover member 34 includes the outlet passage, it is realized that other designs for the housing components could be developed, utilizing the novel and inventive concepts disclosed herein. By way of example, the housing assembly 30 could be in three or more parts wherein the filter support member 32 does not necessarily provide the inlet passage, or the filter support member 32 could be in the form of a cartridge disposed within a housing member which provides the inlet and outlet passages.

The filter support member 32 has a connecting structure 38 and a filter supporting structure or basket portion 40 which depends from the connecting structure 38. The connecting structure 38 includes a generally circular platform 42, an inlet conduit 44 and a pair of latch arms 46. The filter supporting structure or basket portion 40 is integrally formed on an inner side of the platform 42 and the inlet conduit 44 is integrally formed on the outer, opposite side of the platform 42. The inlet conduit 44 has a plurality of ridges 48 thereon so that the aspirator tip 26 (or a hose, if necessary) can be easily secured thereto as shown in FIG. 4. An inlet passage 50 is formed through the inlet conduit 44 and the platform 42.

The latch arms 46 are integrally formed on the outer margins of the platform 42 and are equi-distantly spaced apart from each other. An outer surface of each latch arm 46 is flush with the outer surface of the platform edge. The latch arms 46 are used to "snap-fit" the filter support member 32 and the cover member 34 together, as described herein. Each latch arm 46 includes an enlarged shoulder portion 52 at its inner end which protrudes inwardly towards the basket portion 40 and a finger engaging portion 54 at the outer, opposite end of each latch arm 46. Each latch arm 46 is connected to the outer margin of the platform 42 at approximately the middle of the latch arm 46 and can generally pivot relative to the platform 42. The finger engaging portions 54 have ridges 56 on the outside thereof, so that an operator can easily grasp the portions 54 even when the operator is wearing wet gloves.

The basket portion 40 is disposed about the inner end 58 of the inlet passage 50 and is formed from a base portion 60 and a pair of spaced apart, opposed, bifurcated filter support arms 62. The base portion 60 and support arms 62 are integrally formed with the platform 42. Each support arm 62 commences at the base portion 60 and extends outwardly therefrom and gradually tapers from the base portion 60 to the end of each support arm 62. The end 64 of each support arm 62 is rounded. The support arms 62 are sized so as to fit snugly within the cover member 34 as described hereinbelow. The filter support arms 62 provide a generally cup-shaped frame to which the filter medium 24 is attached, as described herein, to form a generally cup-shaped filter. The support arms 62 may have a plurality of reinforcing ribs 66 thereon to provide strength in the assembly. In addition, as best seen in FIG. 2, base portion 60 includes an aperture 63 for reception of a valve element on gasket member 36, as discussed more fully with regard to FIGS. 4 and 5.

The filter medium 24 which is used in the present invention is a flat or planar sheet or screen and is preferably formed from F.D.A. approved polyester, polyethylene (50 micron) or nylon. The porosity of the filter medium 24 will depend on the application. After a single use, the filter medium 24, along with the remainder of the unit 20, is disposed of in a proper manner.

As shown in FIG. 6, all four edges of the filter medium 24 are hot rolled for a predetermined distance, shown by length 70, and thereafter compressed and heat bonded to prevent frayed edges and loose threads from forming and becoming unraveled and mixed with the collected bone specimens 22. The edges 68 are melted and sealed by hot knife cutting during slitting and roller sealed during the manufacture of the filter medium 24. A suitable agent, such as an adhesive material 76, is applied to the length 70 along one side of each of the four edges 68 of the filter medium 24 so that the filter medium 24 can be releasably secured to the basket portion 40. This process leaves a standard filter mesh thickness 72 in the center of the filter medium 24. Additionally, a plastic film (not shown) can be provided on the opposite side of the filter medium 24 adjacent to the adhesive material 76 and permanently bonded to the opposite side of the filter medium 24. The plastic film would have a window therein so that fluid material can flow through the filter medium 24.

The adhesive 76 that is used in accordance with the present invention is an F.D.A. approved, one-way, one-time use adhesive. A suitable adhesive 76 which is used in accordance with the present invention must be removable after a single use without being able to be readhered. A suitable adhesive material is an adhesive, which, once the filter medium 24 is pulled apart from the basket portion 40, the adhesive function of the adhesive material is lost. For example, a suitable adhesive is a thermally activated adhesive which reliably bonds the filter medium 24 to the basket portion 40 but which, once the filter medium 24 is removed from the basket portion 40, the adhesive material cannot be easily reattached or readhered to the basket portion 40. Thus, the adhesive material used is a single use adhesive and, as such, the filter medium 24 and the unit 20 must be disposed of after a single use. Such an adhesive material may be a hot melt adhesive which is readily available and not difficult to obtain but is manufactured and sold on a proprietary basis. Alternatively, other suitable attaching or securing agents can be used to reliably bond the filter medium 24 to the basket portion 40 and releasably secure the filter medium 24 to the basket portion 40 so long as the attaching or securing means cannot be reattached or resecured to the basket portion 40 after a single use thereby forcing the user to dispose of the filter medium 24 and the unit 20. While the use of adhesive material 76 is described herein for releasably securing the filter medium 24 to the basket portion 40, it is to be understood that the invention is not so limited and other forms of releasable, non-reattachable attaching or securing means could be used. For example, it is envisioned that the filter medium 24 could be releasably secured to the basket portion 40 by a suitable one-time use releasable bonding, welding, heat sealing, double stick tape or by staking.

The long edges of the filter medium 24 are releasably secured to the edges 74 of the support arms 62 and the short edges of the filter medium 24 are releasably secured to the base portion 60 by the adhesive 76. To remove the filter medium 24 from the basket portion 40, the filter medium 24 can be peeled off of the bifurcated frame so that the filter medium 24 can lay flat as shown in FIG. 5. The filter medium can be fully separated from the filter support member 32 or partially separated therefrom. Thereafter, the bone specimens 22 are easily removed from, such as by being scraped off of, the flat sheet of filter medium 24.

The cover member 34 includes a body portion 78 and a outlet conduit 80 attached to the outer end of the body portion 78. The inner, opposite end of the body portion 78 is circular and open. The body portion 78 is formed from a truncated cone section 82 and a section 84 which tapers from the end of the truncated cone section 82 to the outlet conduit 80. The open end of the body portion 78 has a diameter which is identical to that of the platform 42. The outlet conduit 80 has an outlet passage 86 therethrough and a plurality of ridges 88 thereon so that the hose 28 can be easily secured thereto as shown in FIG. 4.

A pair of elongated slots 90 of a predetermined length are formed on the outside of the truncated cone section 82 and are spaced equi-distantly from each other around the truncated cone section 82. Each slot 90 commences at the open end of the truncated cone section 82 and has a raised shoulder 92 along its length. The length of the shoulder 92 is approximately equal to the length of the latch arm 46 between the platform 42 and the shoulder 52. If a gasket member 36 is provided in the unit 20, as described herein, the length of the raised shoulder 92 is slightly less than the length of the latch arm 46 between the platform 42 and the shoulder 52 and the width of the gasket member 36. The elongated slots 90 may have an arrow-shape 94 formed on an end thereof, along with the word "FLOW", to indicate to a user which direction the fluid material flows through the collector unit 20 to aid the user in connecting the unit 20 in the suction line in the correct direction.

The cover member 34 also includes a plurality of mechanical locating ribs 96, preferably four ribs, on the inside of the truncated cone section 82 to assist in holding the filter medium 24 to the filter support member 32. This acts as a safety feature to minimize the possibility of the adhesive 76, which holds the filter medium 24 to the basket portion 40, from prematurely releasing during storage.

The filter support member 32 and the cover member 34 are made by a suitable method, such as molding, and are made of a suitable material, preferably polypropylene or polyethylene plastic. The collector unit 20 is designed to be a one-time use unit, that is, once the collector unit 20 is used on a patient, the unit 20 is disposed of in a proper manner. Since both the filter support member 32 and the cover member 34 are preferably formed from polypropylene or polyethylene plastic, these materials do not lend themselves to heat sterilizing. This acts as a safety feature since it aids in preventing the unit's 20 re-use on other patients. Of course, the unit 20 is sterilized for initial production usage by methods not normally available in a dentist's or physician's offices. It is envisioned, however, that the collector unit 20 could be designed and built for re-sterilization and re-use by using suitable materials, if required.

To secure the filter support member 32 and the cover member 34 together, the basket portion 40 on the member 32 is inserted into the cover member 34 through the open end of the cover member 34. The filter support member 32 is rotated until the latch arms 46 align with the elongated slots 90 on the cover member 34. Thereafter, the filter support member 32 and the cover member 34 are pushed together, such that the latch arms 46 slide along the elongated slots 90 with each of the shoulders 52 sliding along the length of the associated raised shoulder 92 on the truncated cone section 82. Once the latch arm shoulders 52 clear the length of the raised shoulders 92, the latch arm shoulders 52 snap inwardly due to the resiliency of the plastic material of which the latch arms 46 are formed, to secure the cover member 34 and the filter support member 32 together.

When the cover member 34 and the filter support member 32 are secured together, the end of cover member 34 fits snugly against the inner side of the platform. The inner surfaces of the shoulders 52 engage against the inner surfaces of the shoulders 92 and the apexes of the shoulders 52 engage against the bases of the elongated slots 90. The outer surfaces of the latch arms 46 lie flush with the outer surface of the truncated cone section 82. The mechanical locating ribs 96 within the cone section 82 abut against the edges 74 of the filter support arms 62 thereby capturing the filter medium 24 between the filter support arms 62 and the locating ribs 96.

A plurality of radial grip rings 98 are provided on the outside of the cover member 34. As shown, the radial grip rings 98 are provided near the end of the truncated cone section 82 which is closest to the tapered section 84. The grip rings 98 allow an operator to obtain a more secure grip on the cover member 34 with wet hands to hold the collector unit 20 better while unlatching the latch arms 46 to separate the cover member 34 from the filter support member 32.

The gasket member 36 is positioned at the juncture between the filter support member 32 and the cover member 34 when the support member 32 and the cover member 34 are secured together as described hereinabove. The gasket member 36 serves to seal the juncture between the filter support member 32 and the cover member 34 and also provides a form of resiliency which forces the cover member 34 away from the latch arm shoulders 52 on the filter support member 32 to keep the latch arms 46 tightly engaged with the raised shoulders 92 provided on the cover member 34. In addition, the gasket member 36 functions as an integral one-way flapper valve which prevents the use of the collector unit 20, if the unit 20 is assembled in the suction line in the wrong direction. That is, if the collector unit 20 is connected in the suction line in a direction opposite to the desired direction of flow, the gasket member 36 covers and seals the end of the fluid inlet passage 50 so that fluid material can not flow through the collector unit 20. This prevents a user from improperly using the filter/collecting features of the collector unit 20.

The gasket member 36 is formed of a suitable material, such as rubber, and is preferably made of silicone or F.D.A approved 40 durometer polyurethane. The gasket member 36 includes an outer, generally circular portion 100 and a tongue or valve portion 102 which depends inwardly from the outer portion 100. The tongue or valve portion 102 terminates in an enlarged head 104 which has a size that is slightly greater than the size of the end 58 of the fluid inlet passage 50. The outer portion 100 of the gasket member 36 has a diameter which is identical to the diameter of the platform 42 and the open end of the cover member 34. A pair of cutouts 106 are provided along the outer margin of the outer portion 100 which correspond in shape to the inner shape of the latch arms 46.

As best shown in FIGS. 5 and 6, the rubber gasket member 36 is compressed between and positioned at the juncture between the filter support member 32 and the cover member 34. The outer, generally circular portion 100 encircles the base portion 60 of the basket portion 40 on the filter support member 32 and is seated between the latch arms 46 and the base portion 60 of the support arms 62. The tongue or valve portion 102 of the gasket member 36 extends through aperture 63 such that the enlarged head 104 completely covers the end 58 of the fluid inlet passage 50. The length of the latch arms 46 between the platform 42 and the shoulder 52 is slightly smaller than the length of the raised shoulder 92 on the cover member 34 and the width of the gasket member 36 so that when the gasket member 36 is positioned therebetween, the gasket member 36 is compressed.

Normally, the head 104 of the gasket member tongue or valve portion 102 overlays the end 58 of the fluid inlet passage 50 by abutting against the filter support member 32. When the collector unit 20 is assembled in a suction line and when fluid material flows through the collector unit 20 in the proper direction, as shown by the arrow in FIG. 4, the fluid material flows through the fluid inlet passage 50 in the inlet conduit 44, moves the tongue portion 102 of the gasket member 36 out of engagement with the filter support member 32 to move the tongue portion 102 to a position whereby the end 58 of the fluid inlet passage 50 is not covered by the tongue portion 102, as shown by the phantom lines in FIG. 4, to provide a path for the flow of fluid material through the collector unit 20. This allows the fluid material to flow from the inlet conduit 44 into the basket portion 40 of the filter support member 32. Since the support arms 62 and filter medium 24 surround the inlet passage 50, the fluid material can only flow through the filter medium 24. As fluid material flows through the cup-shaped filter medium 24, bone specimens 22 are filtered out of the fluid material and are collected on the filter medium 24 between the bifurcated arms 62. Thereafter, the filtered fluid material flows through the outlet conduit 80 in the cover member 34 and out of the collector unit 20.

After the suctioning procedure is finished, the collector unit 20 can be easily snapped apart so that the dentist or operator can remove the bone specimens 22 from the mesh of the filter medium 24. To snap the unit 20 apart, the operator presses inwardly on the finger engaging portions 54 of the latch arms 46 which causes the shoulders 52 on the opposite ends of the latch arms 46 to disengage from engagement with the raised shoulders 92 on the cover member 34. The plastic material of which the filter support member 32 is formed has sufficient resiliency to easily allow an operator to press the finger engaging portions 54 inwardly to cause the shoulders 52 to disengage from the shoulders 92. Once the shoulders 52 on the latch arms 46 are clear of the raised shoulders 92 on the cover member 34, the filter support member 32 and the cover member 34 can simply be pulled apart from each other. The compression of the elastomeric gasket member 36 aids in unlatching the cover member 34 from the filter support member 32. The ridges 56 on the finger engaging portions 54 of the filter support member 32 and the radial grip rings 98 on the cover member 34 facilitate an operator who is wearing wet gloves in separating the filter support member 32 from the cover member 34.

Once the filter support member 32 and the cover member 34 have been completely separated, the filter medium 24 is peeled off of the basket portion 40 so that the filter medium 24 with the bone specimens 22 thereon can be disposed in a flat orientation as shown in FIG. 5. The filter medium 24 may have a tab 108 thereon which is not attached to the basket portion 40 to facilitate an operator peeling the filter medium 24 off of the basket portion 40 by providing a portion of the filter medium 24 which can be easily grasped and pulled. If the plastic film is provided on the filter medium 24 on the side opposite to that of the releasable adhesive 76, the tab 108 may also be covered by the plastic film. Since the adhesive material 76 or other means used to releasably attach the filter medium 24 to the basket portion 40 is a single use means, the filter medium 24 cannot be reattached or resecured to the basket portion 40.

Once the filter medium 24 is detached from the basket portion 40, or disposed in a flat orientation, as shown in FIG. 5, it is relatively easy for an operator to collect the bone specimens 22 due to the flat nature of the filter medium 24. The bone specimens 22 can be easily scraped off of the flat filter medium 24 for use.

When the collector unit 20 is assembled in a suction line in an incorrect direction, that is in a direction opposite to that shown in FIG. 4, the tongue portion 102 of the gasket member 36 blocks the end 58 of the fluid inlet passage 50 to prevent the flow of fluid material through the collector unit 20. If the unit 20 is connected in the wrong direction, fluid material would flow into the unit 20 through the outlet conduit 80 and then through the filter medium 20. The fluid material would flow up against the head 104 of the gasket member 36 and push the head 104 into sealing engagement with the end 58 of the fluid inlet passage 50. As a result, the fluid material will be prevented from passing through the collector unit 20. Since the fluid material cannot flow through the collector unit 20, it is indicated to an operator that the collector unit 20 is attached in the suction line in the incorrect direction.

The single use adhesive 76 which is used to secure the filter medium 20 to the basket portion 40 prevents the filter medium 20 and the collector unit 20 from being reused. This is important to prevent contamination since the collector unit 20 cannot be reused once the filter medium 20 is removed. This prevents the danger of infecting a second patient with any diseases carried by the first patient.

The novel collector unit 20 of the present invention can be used for other purposes, such as tissue collection or the like, or any other material in a fluid. The filter medium 20 can have a finer mesh or coarser mesh to suit the application. Various features of the present invention can be easily modified if needed for a particular application. For example, the gasket member 36 can be removed from the collector unit 20 to allow for usage of the collector unit 20 in the reverse direction. Furthermore, the filter medium 20 can be permanently affixed to the basket portion 40 if that was required for an application. Moreover, the cover member 34 can also be permanently sealed to prevent removal, if desired.

While a preferred embodiment of the present invention is shown and described, it is envisioned that those skilled in the art may devise various modifications of the present invention without departing from the spirit and scope of the appended claims.

The invention claimed is:

1. A tissue or bone collector unit comprising: a housing assembly including an interior and a filter support member, said housing assembly including fluid inlet and outlet passages, said filter support member including filter supporting structure disposed in said housing interior for supporting a substantially planar, porous filter medium in a reverse bend configuration such that said filter medium is disposed across and spans said inlet passage, a porous filter medium removably secured to said filter supporting structure in said reverse bend configuration to span said inlet passage such that fluid material passing through said collector unit must pass through said porous filter medium which will filter out any bone or tissue specimens in said fluid material said porous filter medium being removable from said filter supporting structure for positioning in a flat-orientation to facilitate the removal of bone or tissue specimens from said porous filter medium.

2. A collector unit as defined in claim 1, wherein said structure for supporting said filter medium comprises a pair of spaced-apart, opposed filter support arms.

3. A tissue or bone collector unit comprising: a housing assembly including an interior and a filter support member, said housing assembly including fluid inlet and outlet passages, said filter support member including filter supporting structure comprising a pair of spaced-apart, opposed filter support arms disposed in said housing interior for supporting a porous filter medium disposed across a portion of said inlet passage, a porous filter medium removably secured to said filter support arms to span said inlet passage such that fluid material passing through said unit must pass through said porous filter medium which will filter out any bone or tissue specimens in said fluid material, said porous filter medium being removable from said filter support arms for positioning in a flat-orientation to facilitate the removal of bone or tissue specimens from said porous filter medium, said filter medium being partially or fully removed from said filter support arms to lie in said flat-orientation.

4. A tissue or bone collector unit comprising: a housing assembly including an interior and a filter support member, said housing assembly including fluid inlet and outlet passages, said filter support member including filter supporting structure comprising a pair of spaced-apart, opposed filter support arms disposed in said housing interior for supporting a porous filter medium disposed across a portion of said inlet passage, a porous filter medium removably secured to said filter support arms to span said inlet passage such that fluid material passing through said unit must pass through said porous filter medium which will filter out any bone or tissue specimens in said fluid material, said porous filter medium being removable from said filter support arms for positioning in a flat-orientation to facilitate the removal of bone or tissue specimens from said porous filter medium, said filter medium further including a tab portion which is not secured to said filter support arms for facilitating the removal of the filter medium from the filter support arms.

5. A collector unit as defined in claim 1, further including a cover member, said filter support member being mountable within said cover member and further including structure for releasably securing said cover member and said filter support member together.

6. A collector unit as defined in claim 5, wherein said structure for releasably securing said cover member and said filter support member together comprises latch arms which are connected to said filter support member and snap over said cover member.

7. A collector unit as defined in claim 6, wherein each of said latch arms on said filter support member includes a shoulder portion thereon which engages with a raised shoulder formed in a slot on said cover member to releasably secure said cover member and said filter support member together, said shoulder portion being movable out of engagement with said raised shoulder so as to enable said cover member and said filter support member to be separated from each other.

8. A collector unit as defined in claim 7, wherein each of said latch arms includes a finger engaging portion thereon which can be moved to move said shoulder portion out of engagement with said raised shoulder.

9. A collector unit as defined in claim 1, wherein said housing assembly further includes a cover member which includes said outlet passage, and said filter support member includes said inlet passage.

10. A collector unit as defined in claim 9, wherein said filter support member is received within said cover member and further including operable latch structure for maintaining said filter support member and said cover member in engagement.

11. A collector unit as defined in claim 1, further including a one-way valve positioned between said fluid inlet passage and said filter medium for only allowing fluid material to flow in one direction through said housing assembly.

12. A collector unit as defined in claim 11, wherein said one-way valve comprises a gasket member associated with said fluid inlet passage which normally blocks a flow of fluid material through said inlet passage and can be moved out of association with said fluid inlet passage to provide a path for the flow of fluid material through said housing assembly.

13. A collector unit as defined in claim 12, wherein said housing assembly includes a cover member and wherein said gasket member includes an outer portion which is positioned between said filter support member and said cover member when said filter support member and said cover member are secured to each other and a tongue portion which depends inwardly from said outer portion and normally blocks the fluid inlet passage and can be moved out of association with said fluid inlet passage to provide a path for the flow of fluid material through said housing assembly.

14. A tissue or bone collector unit comprising: a housing assembly including an outer cover member and an inner filter support member mountable within said cover member, fluid inlet and outlet passage structure provided by said housing assembly, said filter support member including a pair of axially disposed, spaced-apart, opposed filter support arms for supporting a porous filter medium disposed about an inner portion of said inlet passage, a porous filter medium removably secured to said filter support arms to span said fluid inlet passage such that fluid material passing through said housing assembly must pass through said porous filter medium which will filter out any bone or tissue specimens from the fluid material, said porous filter medium being removable from said filter support arms for positioning in a flat-orientation to facilitate the removal of bone or tissue specimens from said porous filter medium.

15. A collector unit as defined in claim 14, further including latch arms for releasably securing said cover member and said filter support member together.

16. A collector unit as defined in claim 15, wherein said latch arms are connected to said filter support member and each said latch arm includes a finger engaging portion and a shoulder portion thereon, each said shoulder portion engaging with a raised shoulder formed in a slot in said cover member to releasably secure said cover member and said filter support member together, said shoulder portion being movable out of engagement with said raised shoulder so as to enable said cover member and said filter support member to be separated from each other so that said filter medium can be removed from said filter support member, said finger engaging portion being movable to move said shoulder portion out of engagement with said raised shoulder.

17. A collector unit as defined in claim 16, wherein said finger engaging portion includes ridges thereon.

18. A collector unit as defined in claim 17, wherein said cover member includes a plurality of rings thereon.

19. A collector unit as defined in claim 14, wherein said filter medium further includes a tab portion which is not secured to said filter support arms for facilitating the removal of the filter medium from the filter support arms.

20. A collector unit as defined in claim 14, further including a one-way valve positioned between said fluid inlet passage and said filter medium for only allowing fluid material to flow in one direction through said housing assembly.

21. A collector unit as defined in claim 20, wherein said one-way valve comprises a gasket member, said gasket member including an outer portion which is positioned between said filter support member and said cover member when said filter support member and said cover member are secured to each other and a tongue portion which depends inwardly from said outer portion and normally blocks the fluid inlet passage and can be moved out of association with said inlet passage to provide a path for the flow of fluid material through said housing assembly.

22. A tissue or bone collector structure comprising: a housing including a mounting member, a porous filter medium derived from a flat sheet of stock and, said porous filter medium being removably affixed to said mounting member and non-reattachable to said mounting member after said filter medium is detached from said mounting member, said porous filter medium being detachable from said mounting member to lie in a flat orientation; and means for removably affixing said filter medium to said mounting member, said filter medium being non-reattachable to said mounting member after said filter medium is detached from said mounting member.

23. A tissue or bone collector structure comprising: a housing, a porous filter medium derived from a flat sheet of stock, said filter medium being removably affixed to said housing and non-reattachable to said housing after said filter medium is detached from said housing, said housing including a mounting member comprising a pair of support arms, said filter medium being removably affixed to and wrapped around said support arms and removable from said support arms to lie in a flat orientation, said filter medium being non-reattachable to said support arms after said filter medium is detached from said mounting member.

24. A tissue or bone collector structure comprising: a housing, a porous filter medium derived from a flat sheet of stock, said porous filter medium being removably affixed to said housing and non-reattachable to said housing after said porous filter medium is detached from said housing, said porous filter medium being detachable from said housing to lie in a flat orientation, and an attaching agent for removably affixing said filter medium to said housing, said attaching agent being non-reattachable to said housing after said filter medium is detached from said housing.

25. A collector structure as defined in claim 24, wherein said attaching agent is an adhesive material.

26. A tissue or bone collector structure comprising: a housing having an inlet, a porous filter medium derived from a flat sheet of stock and being removably affixed to said housing and non-reattachable to said housing after said porous filter medium is detached from said housing, said porous filter medium being detachable from said housing to lie in a flat orientation, said porous filter medium being removably affixed to said housing in a reverse bend configuration and spanning said inlet of said housing.

27. A tissue or bone collector unit comprising: a housing assembly including an interior and a filter support member, said housing assembly including fluid inlet and outlet passages, said filter support member including filter supporting structure comprising a pair of spaced-apart, opposed filter support arms disposed in said housing interior for supporting a porous filter medium disposed across said inlet passage, a porous filter medium affixed to said filter support arms to span said inlet passage such that fluid material passing through said unit must pass through said porous filter medium which will filter out any bone or tissue specimens in said fluid material.

28. A tissue or bone collector unit as defined in claim 27, wherein said porous filter medium is affixed to said housing assembly in a reverse bend configuration and spans said inlet passage of said housing assembly.

* * * * *

UNITED STATES PATENT AND TRADEMARK OFFICE
CERTIFICATE OF CORRECTION

PATENT NO.    : 5,766,134
DATED         : June 16, 1998
INVENTOR(S)   : Stephen P. Lisak and Larry L. Young It is certified that error appears in the above-indentified patent and that said Letters Patent is hereby corrected as shown below:

CLAIMS

Column 10, Lines 39-40   "a portion of said" should be -- said --
Column 10, Lines 56-57   "a portion of said" should be -- said --

Signed and Sealed this

Twelfth Day of January, 1999

Attest:

Attesting Officer          *Acting Commissioner of Patents and Trademarks*